(12) United States Patent
Sokel et al.

(10) Patent No.: US 8,857,035 B2
(45) Date of Patent: *Oct. 14, 2014

(54) METHOD FOR COLD LOADING AN ARTICLE

(71) Applicant: Machine Solutions, Inc., Flagstaff, AZ (US)

(72) Inventors: Justin Sokel, Flagstaff, AZ (US); Paul Reiss, Flagstaff, AZ (US)

(73) Assignee: Machine Solutions, Inc., Flagstaff, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/795,601

(22) Filed: Mar. 12, 2013

(65) Prior Publication Data

US 2013/0213520 A1 Aug. 22, 2013

Related U.S. Application Data

(62) Division of application No. 13/600,457, filed on Aug. 31, 2012, now Pat. No. 8,484,822, which is a division of application No. 12/229,566, filed on Aug. 25, 2008, now Pat. No. 8,256,087.

(60) Provisional application No. 60/966,018, filed on Aug. 24, 2007.

(51) Int. Cl.
*B21D 39/00* (2006.01)
*A61F 2/95* (2013.01)

(52) U.S. Cl.
CPC ............ *A61F 2/95* (2013.01); *A61F 2002/9522* (2013.01)
USPC ................................................ 29/508; 141/2

(58) Field of Classification Search
CPC .............. A61F 2002/9522; A61F 2/95; A61F 2002/30677
USPC .................................................. 29/508; 141/2
See application file for complete search history.

(56) References Cited

U.S. PATENT DOCUMENTS

| | | | |
|---|---|---|---|
| 6,543,155 B2 | 4/2003 | Horigane | |
| 2007/0293930 A1* | 12/2007 | Wang et al. | 623/1.11 |
| 2008/0045632 A1* | 2/2008 | Jo et al. | 523/400 |
| 2008/0072653 A1* | 3/2008 | Gillick et al. | 72/402 |

* cited by examiner

*Primary Examiner* — David Bryant
*Assistant Examiner* — Ruth G Hidalgo-Hernande
(74) *Attorney, Agent, or Firm* — Skinner and Associates; Joel Skinner

(57) ABSTRACT

A method of loading an article, such as a self-expanding stent, into a structure, such as a delivery catheter, including the steps of chilling the article to a predetermined temperature, reducing article size a predetermined amount, inserting fluid into the article, whereby the fluid forms a substantially solid plug with respect to the article, and moving the frozen article. Also provided is an apparatus for loading an article into a structure including: an article size reduction element, a chiller connected to the size reduction element, a cold source communicatively connected to the chiller, and a fluid supply communicatively connected to the size reduction element.

13 Claims, 4 Drawing Sheets

METHOD FOR COLD LOADING AN ARTICLE

CROSS-REFERENCE TO RELATED APPLICATIONS, IF ANY

This application is a divisional of U.S. application Ser. No. 13/600,457, filed Aug. 31, 2012, status pending, which is a divisional of US Application Serial No. 12/229,566, filed Aug. 25, 2008, which issued as U.S. Pat. No. 8,256,087 on Sep. 4, 2012, which claims the benefit under 35 U.S.C. §119 (e) of U.S. Provisional Patent Application Ser. No. 60/966,018, filed Aug. 24, 2007, which are hereby incorporated by reference.

37 C.F.R. §1.71(e) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to a method and apparatus for processing, moving and loading materials, articles, apparatus or structures utilizing cooling means or steps. Particularly, the invention relates to a method of cooling and processing an article to facilitate loading into another article, structure or space. Most particularly, the invention relates to a method and apparatus for loading an article such as a medical stent, stent graft or the like (particularly self-expanding stents or other articles) into medical catheters, tubes, carriers, housings and the like.

2. Background Information

The state of the art includes stents, stent grafts and the like, loaders for such articles, and crimpers. Included in known stents are self-expanding type stents. Included in crimpers are crimpers which have means for cooling certain parts of the crimper.

Self-expanding stents are fragile precision articles used in intravascular (including but not limited to cardiac vascular procedures) medical procedures, typically therapeutic procedures. They are comprised of a fine mesh structure with a tubular configuration of a predetermined length. The stent tube has a central lumen which serves as a space for holding the stent. They are typically made of a shape memory material such as NITINOL. Manufactured stents are loaded into a deployment device such as a catheter typically by temporarily reducing the diameter of the stent (for example by crimping or otherwise radially compressing them) to slightly less than that of the deployment catheter lumen, and then inserting the reduced diameter stent into an open end of the deployment catheter lumen (typically the distal end of the deployment catheter). In typical use, the deployment catheter is inserted into and moved through the vasculature by well known percutaneous and fluoroscopic procedures. At the appropriate therapeutic location, a control piece in the catheter is actuated to push the stent out of the distal end. Once the stent is out of the catheter lumen, and no longer constrained by the catheter, the shape memory properties of the stent cause it to expand naturally in the vasculature.

Loading of the stent from the diameter reduction means to the deployment catheter is important and challenging. Known methods of loading self-expanding stents into delivery catheters include "push loading" and "inch-worm loading." The stent is difficult to handle and move anywhere by virtue of its small size, and flexibility. Longitudinal movement is particularly difficult, especially for long stents. And movement into the small lumen of the catheter is most particularly difficult. Also, loading must take place as the stent seeks to expand at any time and point where it is not radially constrained by the reduction or deployment means.

In summary, the known existing technology is believed to have limitations and shortcomings and a need exists for the present invention.

All US patents and patent applications, and all other published documents mentioned anywhere in this application are incorporated by reference in their entirety.

BRIEF SUMMARY OF THE INVENTION

The invention provides an apparatus and method for cold loading an article, in particular a self-expanding stent, into a structure or space, in particular a stent deployment catheter, which is practical, reliable, accurate and efficient, and which is believed to fulfill the need and to constitute an improvement over the background technology.

The apparatus and method are useful for loading a fragile, delicate and/or precision article into a tight space, for example spaces (in structures for example) where the dimensions of the space are only slightly larger, or even the same or smaller, than the dimensions of the object. The invention is particularly useful for loading a self-expanding stent into a deployment catheter. The invention is most particularly useful for loading long (equal to or greater than 100 mm for example) self-expanding stents into deployment catheters.

In one aspect, the invention provides a method of processing an article or apparatus including the steps of applying a frozen support matrix to at least a portion of the article; processing the supported article; and removing the frozen matrix from the article.

In another aspect, the invention provides a method of processing an article or apparatus including the steps of:
a. applying a frozen matrix to at least a portion of the article or apparatus;
b. processing the matrix applied article or apparatus, whereby during processing, the article or apparatus is supported by the matrix; and
c. removing the matrix from the article or apparatus after processing.

The step of applying a frozen support matrix to at least a portion of the article or apparatus preferably includes the sub-steps of providing the article or apparatus, cooling the article or apparatus to a predetermined temperature; and applying a fluid to the article or apparatus, the fluid freezing at or below the predetermined temperature.

And yet a further aspect, the invention provides method for loading a self-expanding stent into a deployment catheter, including the steps of:

a. compressing the stent to a diameter less than the diameter of the lumen of the deployment catheter;
b. applying a support matrix to the stent by cooling the stent to a predetermined cold temperature and applying a fluid to the stent, whereby the fluid freezes to form the matrix embedding the stent;
c. pushing the stent and matrix into the stent deployment catheter lumen; and
d. a removing the matrix from the inserted stent by sublimation.

The aspects, features, advantages, benefits and objects of the invention will become clear to those skilled in the art by reference to the following description, claims and drawings.

DETAILED DESCRIPTION

The method and apparatus of the invention crimps and loads, self-expanding Nitinol stents into catheter delivery systems. They provide consistent loading of long fragile stents without causing damage to these precision medical products. The invention is particularly useful for loading long (>100 mm) stents.

The method and apparatus of the present invention reduces the diameter of the stent, cools the stent, applies a fluid to the stent whereby the fluid freezes and creates a substantially solid support structure which engages the stent. The stent and support structure is then moved into the deployment means. The support structure sublimates or evaporates leaving the stent in the deployment means.

1. APPARATUS OF THE INVENTION

Figure 1:
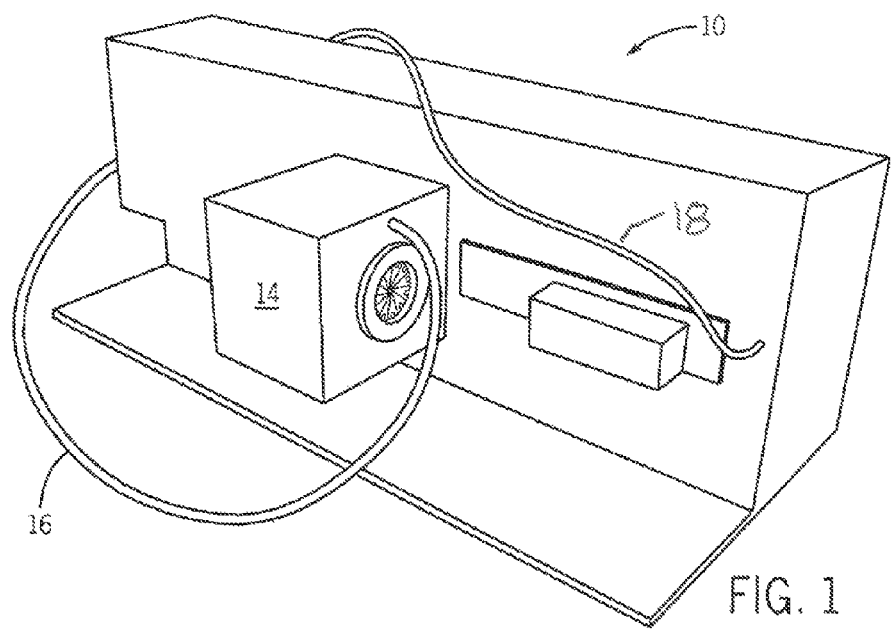
FIG. 1 shows an embodiment of the apparatus for cold loading articles of the present invention.

Referring to FIG. 1, a preferred embodiment of the apparatus 10 for cold loading an article comprises a crimping head 12, a chiller 14, a Nitrogen gas supply 16, a fluid supply 18, and a stent 20. The crimping head 12 is preferably an SC900/950 manufactured by Machine Solutions, Inc. (MSI) of Flagstaff, Ariz., USA. Other crimpers consistent with the invention are disclosed in U.S. Pat. Nos. 6,629,350 and 6,968,607 to Motsenbocker. The crimp head 12 preferably has 1-14 mm×130 mm, Nickel coated stainless steel tips. The chiller 14 is preferably an MSI LN2 Chiller with a single circuit. The liquid N source 16 is preferably a 160 L Dewar with 22 psi liquid output which is connected to the chiller 14. The chiller 16 is internally valved. The fluid supply 18 is preferably a 50 lb regulated bottle which is connected to the crimping head 12. The preferred gas is carbon dioxide ($CO_2$). The exemplary stent product 20 shown is an 8 mm×100 mm Nitinol stent.

The crimp head 12 preferably has a capacity to cool down to approximately −100 degrees C. The crimp head 12 preferably has the capacity to crimp down to approximately 2 mm. The Nitrogen cooling supply 16 delivers liquid N at approximately 22 psi. The gas supply supplies CO2 at between 20-35 psi.

In summary, the invention provides an apparatus for loading an article into a structure including: an article size reduction element, a cooler connected to the size reduction element, a cold source communicatively connected to the cooler, and a fluid supply communicatively connected to the size reduction element.

2. METHOD OF THE INVENTION

Figure 2A:
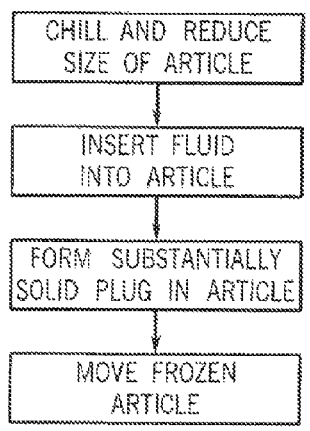
FIG. 2A is a flow chart of an embodiment of the method of cold loading an article of the present invention.

Referring to FIG. 2a, an embodiment of the basic method of the present invention comprises the steps of:
Reduce article size predetermined amount, or otherwise pre-process the article.
Chill stent or article to predetermined temperature.
Insert or otherwise supply fluid to the article.
Wait for fluid to form a substantially solid plug with respect to the article.
Move the frozen article.

Figure 2B:
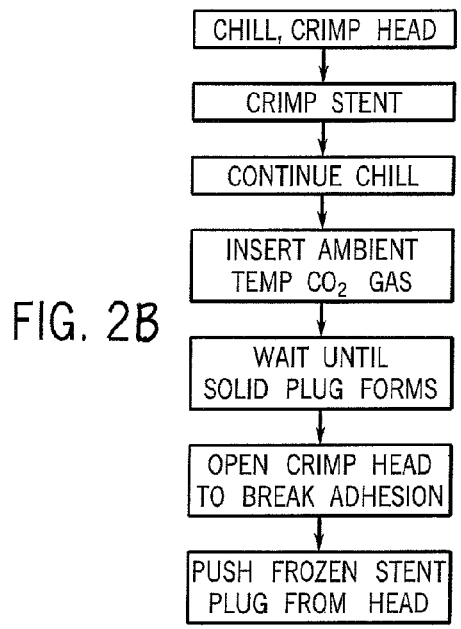
FIG. 2B is a flow chart of another embodiment of the method of cold loading an article of the present invention.
Figure 6:
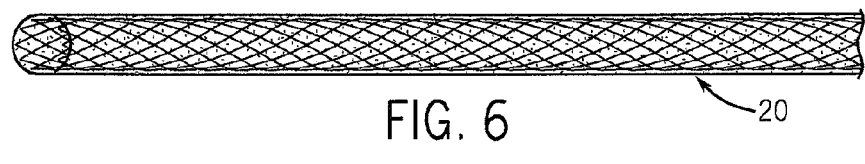
FIG. 6 shows the cold processed self-expanding stent output by the assembly.

Referring to FIG. 2b, a preferred embodiment of a detailed method of the present invention comprises the steps of:
1. Chill entire crimp head 12 to below −30° C. using cold gaseous nitrogen to avoid internal frost buildup.
2. Crimp Stent 20 to 2 mm diameter (normal final crimp diameter).
3. Continue to chill crimp head 12 until segment tips temperature drops below −78.5° C., which is the freezing point of $CO_2$.
4. Insert ambient temperature $CO_2$ gas, at 20 psi into one end of the crimp head aperture.
5. Wait for the $CO_2$ gas to form a solid dry ice plug 22 throughout the stent 20 through vapor deposition, as shown in FIG. 6.
6. Open the crimp head 12 slightly to help break loose any adhesion between the dry ice plug and the segment tips.
7. Push the frozen stent plug 12 out of the crimp head 12.

Figure 3:
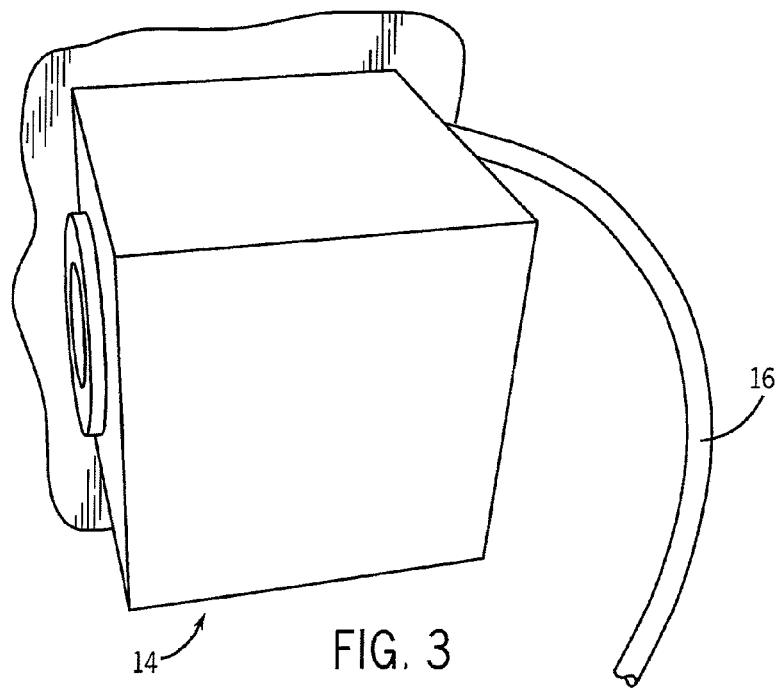
FIG. 3 shows an embodiment of a processing and loading assembly for use with the system of the invention.
Figure 4:
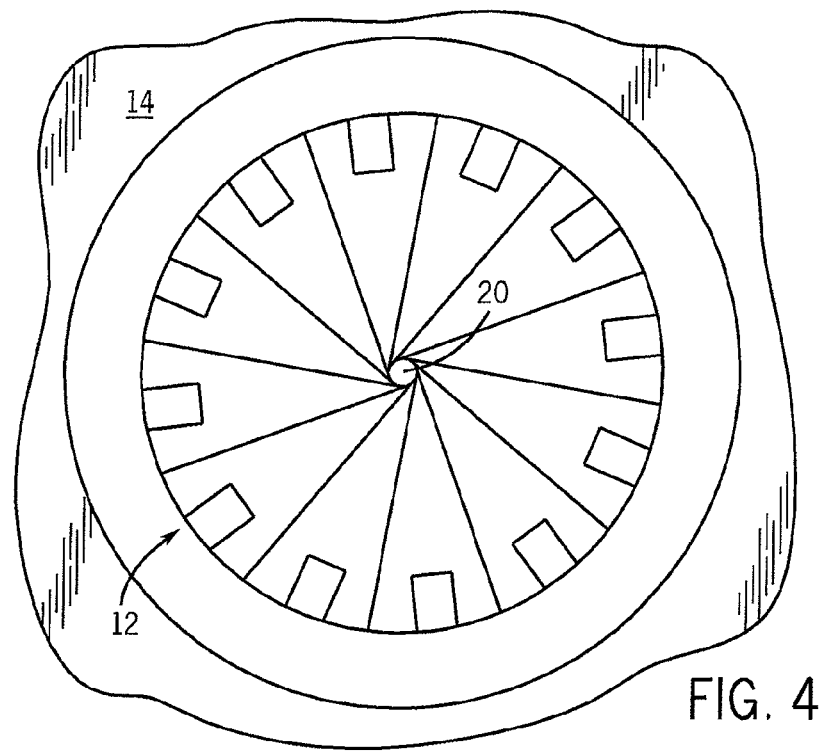
FIG. 4 shows an end view of a portion of the processing and loading assembly of FIG. 3.
Figure 5:
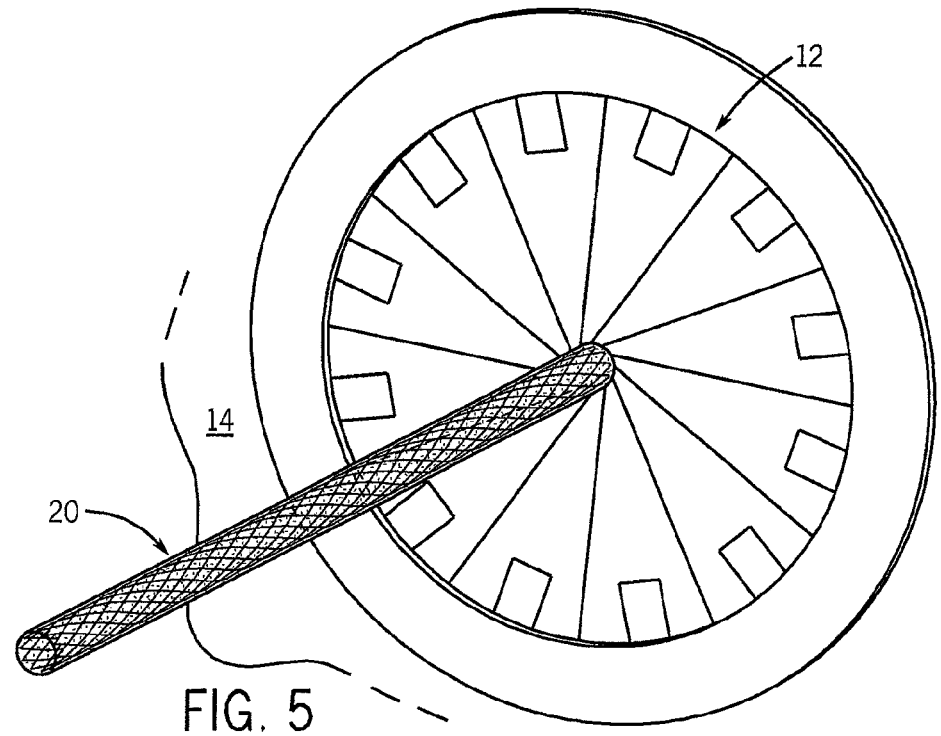
FIG. 5 shows an exemplary article, a self-expanding stent, processed by the system and assembly of FIGS. 1-4, the stent emerging from the assembly portion shown in FIG. 4 for loading.

Cooling time for initial crimp head cooling from ambient temperature to −100° C. is approximately 30 mins using low flow LN2 Chiller. The same stent was processed 3 times as follows:
1. Cycle 1, 2 mm crimp diameter, good ice plug formation, easy plug release from crimp head
2. Cycle 2, 2 mm crimp diameter, good ice plug formation, easy plug release from crimp head
3. Cycle 3, 3 mm crimp diameter, good ice plug formation, slight problem with plug release from crimp head due to previous buildup of $CO_2$ deposits For the 3 mm crimp diameter plug, $CO_2$ ice formation is visible from within the crimped stent 20 over a period of about 1.5 minutes. Ice formation starts at the stent and crimp aperture surface and forms inwardly radially, in a substantially even fashion. An input pressure of 35 psi is utilized for the gaseous $CO_2$ input. Referring to FIGS. 4 and 5, frost does not substantially form inside the crimp head 12 during processing. Referring to FIG. 3, frost accumulates on the portions of the crimp head 12 exposed to the ambient atmosphere.

For the 2 mm crimp diameters the stent 20 is physically restrained from opening (due to low amounts of retained elastic stiffness by the Nitinol) momentarily until the warm ambient temperature caused the outer $CO_2$ surface to sublimate away, thus releasing the stent struts. While not intending to limit the invention, it is believed that the $CO_2$ gas penetrates the spaces between adjacent stent struts and between the stent 20 and crimp segment tips of the crimper 12 before freezing.

Figure 7:
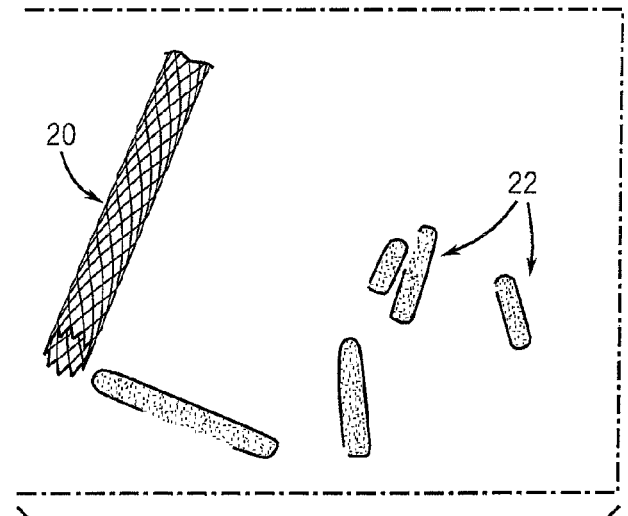
FIG. 7 shows a self-expanding stent article and CO2 plug portions removed therefrom.
Figure 8:
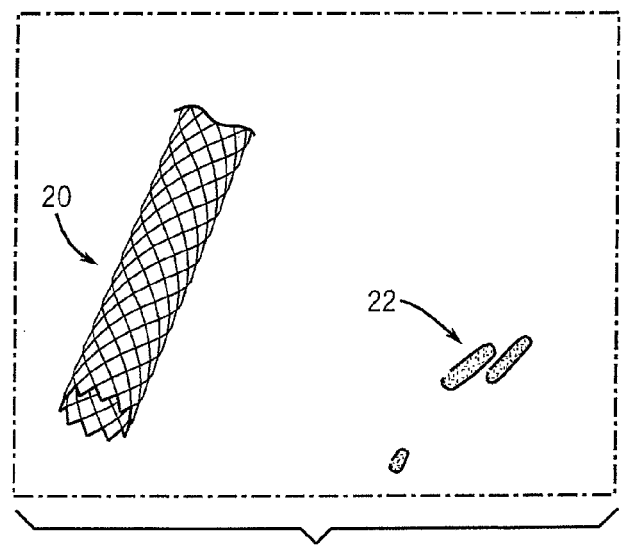
FIG. 8 shows a self-expanding stent article and CO2 plug portions removed therefrom approximately 30 seconds after that shown in FIG. 7, wherein the plug portions are substantially smaller due to sublimation.

Referring again to FIG. 6, the 3 mm crimp diameter processing shows longer-lived encapsulation after the stent 20 is removed from the crimp head 12. Referring to FIGS. 7 and 8, after removing the stent plug from the crimp head 12, rod-shaped portions 22 of the dry ice are clearly visible inside the stent 20. The dry ice sublimates away leaving no trace as the dry ice warms above −78.5° C.

The method encapsulates the crimped Nitinol stent in a pure $CO_2$ (dry ice) "plug". This allows the use of higher axial push-loading forces with minimal loading failures and minimal stent damage. To load, the frozen, encapsulated stent is pushed into the catheter lumen. Pushing may be accomplished with considerable force without causing damage. Dry ice plugs form around the crimped stent 20 with minimal tuning. Dry ice that remains within the stent during loading facilitates keeping the Nitinol below its transformation temperature as it travels into the delivery system. Cycle time, frost accumulation, and plug release are readily optimizable. The method is useable with a variety of stent diameters, lengths, material thicknesses and stent types.

In summary, the invention provides a method of loading an article into a structure including the steps of cooling the article to a predetermined temperature, reducing article size a predetermined amount, inserting fluid into the article, whereby the fluid forms a substantially solid plug with respect to the article, and moving the frozen article.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. A method of loading a stent having a tubular body and a central lumen, into a deployment catheter, comprising the steps of:
   a. compressing the stent to a diameter less than the diameter of the lumen of the deployment catheter;
   b. applying a support matrix to the steal by cooling the stent to a predetermined cold temperature and applying a fluid to the stent, whereby the fluid freezes to form the matrix embedding the stent across the central lumen of the stent, wherein the predetermined temperature is equal to or less than minus 78.5 C, and wherein the matrix comprises frozen $CO_2$;
   c. pushing the stent and matrix into the stent deployment catheter lumen, whereby the matrix supports the tubular body of the stent; and
   d. removing the matrix from the inserted stent by sublimation.

2. The method of claim 1, wherein the stent is fragile.

3. The method of claim 1, wherein the stent has plural shape states.

4. The method of claim 1, wherein the stent is a self-expanding stent having a predetermined expanded diameter and which is radially compressible to a diameter less than that of the expanded diameter.

5. The method of claim 4, wherein the self-expanding stent has a predetermined length which is greater than 100 mm.

6. The method of claim 4, wherein the self-expanding stent has at least first and second shape states, and wherein the stent is provided at a first shape state, and wherein the stent changes seeks to change to the second shape state after removing the frozen matrix from the article or apparatus.

7. The method of claim 6 wherein the stent is a self-expanding stent having a predetermined expanded diameter and which is radially compressible to a diameter less than that of the expanded diameter, and wherein the stent is provided compressed, at a diameter less than its expanded diameter; and wherein to stent seeks to change to its expanded diameter after removing the frozen matrix from the stent.

8. The method of claim 1, wherein compressing is crimping.

9. The method of claim 8, wherein the step of cooling comprises contacting the stent with one or more cooled surfaces for a predetermined time.

10. The method of claim 9, wherein the cooled surfaces are part of a crimper.

11. The method of claim 10, wherein the step of crimping is accomplished before fully cooling the stent.

12. The method of claim 4, wherein the self-expanding stent has a predetermined expanded diameter and the stent deployment catheter lumen has a diameter less than that of the expanded diameter of the stent.

13. The method of claim 1, wherein the step of removing the matrix from the stent after processing is accomplished by sublimation while the stent is disposed within the stent deployment catheter lumen.

* * * * *